United States Patent
Schröer et al.

(10) Patent No.: US 11,653,085 B2
(45) Date of Patent: May 16, 2023

(54) IMAGE RECORDING SYSTEM, WHICH SUGGESTS SITUATION-DEPENDENT ADAPTATION PROPOSALS, AND ASSOCIATED IMAGE RECORDING METHOD

(71) Applicant: SCHÖLLY FIBEROPTIC GMBH, Denzlingen (DE)

(72) Inventors: Stefan Schröer, Freiburg (DE); Matthias Kühn, Freiburg (DE); Alexander Köhler, Freiburg (DE); Daniel Härter, Emmendingen (DE); Joachim Jauss, Rheinhausen (DE)

(73) Assignee: SCHÖLLY FIBEROPTIC GMBH, Denzlingen (DE)

( * ) Notice: Subject to any disclaimer, the term of this patent is extended or adjusted under 35 U.S.C. 154(b) by 193 days.

(21) Appl. No.: 16/925,722

(22) Filed: Jul. 10, 2020

(65) Prior Publication Data
US 2021/0014410 A1    Jan. 14, 2021

(30) Foreign Application Priority Data
Jul. 10, 2019  (DE) ..................... 10 2019 118 750.8

(51) Int. Cl.
*A61B 17/32* (2006.01)
*H04N 23/62* (2023.01)
(Continued)

(52) U.S. Cl.
CPC ........... *H04N 23/62* (2023.01); *A61B 1/0004* (2022.02); *A61B 1/00045* (2013.01);
(Continued)

(58) Field of Classification Search
None
See application file for complete search history.

(56) References Cited

U.S. PATENT DOCUMENTS

| | | |
|---|---|---|
| 10,776,902 B2 * | 9/2020 | Bergen ................. G06V 10/507 |
| 2015/0065803 A1 * | 3/2015 | Douglas ........... A61B 1/000096 |
| | | 600/200 |

(Continued)

FOREIGN PATENT DOCUMENTS

| | | |
|---|---|---|
| WO | 2016168838 A2 | 10/2016 |
| WO | 2018017625 A1 | 1/2018 |

OTHER PUBLICATIONS

Digitalkamera mit Wechselobjektiv; ILCE-6500 a6500; Auto. Objektrahm. (Standbild).

(Continued)

*Primary Examiner* — Howard D Brown, Jr.
(74) *Attorney, Agent, or Firm* — Grogan, Tuccillo & Vanderleeden, LLP (57) ABSTRACT

To simplify the use of a functional scope of a medical image recording system, for example an endoscopy system, a method is proposed in which an image processing unit of the image recording system recognizes predefined image recording situations on the basis of an image sequence recorded using an image sensor of the image recording system and in response thereto proposes an adaptation to a user that results in an improved display and/or an improved recording of the image sequence in the respective recognized image recording situation. The adaptation can relate here to an algorithm, using which the image sequence is processed after the recording, and/or an image recording method currently used to generate the image sequence.

18 Claims, 3 Drawing Sheets

(51) Int. Cl.
    *H04N 5/77*      (2006.01)
    *A61B 1/05*      (2006.01)
    *A61B 1/045*     (2006.01)
    *A61B 1/00*      (2006.01)
    *A61B 1/06*      (2006.01)
    *H04N 23/60*     (2023.01)
    *H04N 23/80*     (2023.01)

(52) U.S. Cl.
    CPC .... *A61B 1/00055* (2013.01); *A61B 1/000095* (2022.02); *A61B 1/045* (2013.01); *A61B 1/05* (2013.01); *A61B 1/0653* (2013.01); *H04N 5/77* (2013.01); *H04N 23/64* (2023.01); *H04N 23/80* (2023.01)

(56) References Cited

U.S. PATENT DOCUMENTS

| | | | |
|---|---|---|---|
| 2015/0208900 A1* | 7/2015 | Vidas | A61B 1/0615 348/74 |
| 2016/0156822 A1* | 6/2016 | Iwasaki | A61B 1/0655 348/68 |
| 2019/0201046 A1* | 7/2019 | Shelton, IV | A61B 1/051 |

OTHER PUBLICATIONS

Dayou Jiang and Jongweon Kim; A Scene Change Detection Framework Based on Deep Learning and Image Matching; Advanced Multimedia and Ubiquitous Engineering, Lecture Notes in Electrical Engineering 518, pp. 623-629; 2019.

Office Action from corresponding DE Application No. 10 2019 118 750.8 dated Apr. 15, 2020.

* cited by examiner

IMAGE RECORDING SYSTEM, WHICH SUGGESTS SITUATION-DEPENDENT ADAPTATION PROPOSALS, AND ASSOCIATED IMAGE RECORDING METHOD

CROSS REFERENCE TO RELATED APPLICATION

This application claims priority to German Patent Application No. 10 2019 118 750.8 filed on Jul. 10, 2019, which is hereby incorporated by reference for all that is disclosed as though fully set forth herein.

FIELD OF THE INVENTION

The invention relates to an image recording method, in which an image sequence, in particular in the form of a video image datastream, is recorded using an image sensor of a medical image recording system, for example, an endoscope, a digital microscope, or an exoscope, wherein the image sequence is subjected to an image processing algorithm even before it is displayed on the display unit in order to improve the display of the image sequence.

The invention furthermore relates to an associated medical image recording system, comprising an image sensor for recording an image sequence and a controller for controlling an image processing algorithm, which is applied to the image sequence in order to improve a display of the image sequence on a display unit.

Such a medical image recording system can in particular be designed as an endoscopy system, having an endoscope which has said image sensor. This system can in particular be designed as a video endoscopy system. Other medical imaging systems that can benefit from the invention are, for example, exoscopes or digital microscopes.

BACKGROUND OF THE INVENTION

A large number of image processing algorithms are used today in modern endoscopy in order to improve the display of images which are recorded with an endoscope, i.e., in particular of video images. This includes functions such as narrow band imaging (NBI) or special algorithms such as selective color enhancement (SCE), which are used to improve the image contrast. Further image parameters that can be improved by such algorithms are, for example, a color spectrum, an edge steepness for improved recognition of structures or an image sharpness or a noise component in the respective image. Noise suppression algorithms or filter algorithms can also be used for this purpose.

Such functions can often significantly improve the image quality, for example an image contrast, particularly in medical applications, as a result of which, for example, the display of blood vessels for diagnosis can be improved.

In practice, however, the use of such algorithms is often unsatisfactory for a user of the endoscopy system, since settings have to be performed in complex menu structures for optimum display of the endoscopically recorded images in order to optimally match the respective algorithm to the respective application. In addition, other settings, such as the illumination currently used for imaging, may have to be adapted depending on the situation of the examination.

All of this leads to an enormously time-consuming adjustment effort, which prevents a user from actually working with the endoscope. In many cases, the user finally helps himself by not doing many adjustments necessary for optimal imaging simply for reasons of time, in order to be able to concentrate on his actual examination work. As a result, however, the actually existing functional scope of the endoscopy system is not fully utilized for the benefit of the patient.

SUMMARY OF THE INVENTION

The invention is therefore based on the object of providing an image recording method and an associated medical image recording system which improves the operation in such a way that the full functional scope can actually be used in practice.

To achieve this object, the features of claim 1 are provided according to the invention in an image recording method. In particular, according to the invention, to achieve the object in a method of the type mentioned at the outset, it is proposed that the recorded image sequence is evaluated in a computer-implemented manner and that, depending on an image-recording situation recognized by means of the computer-implemented image evaluation, an adaptation of the image processing algorithm to a user and/or an image recording method used when recording the image sequence is proposed.

The computer-implemented evaluation of the image sequence can preferably be carried out by the medical image recording system itself. Furthermore, the second method step can in particular be designed in such a way that said image recording system automatically proposes said adaptation to a user of the endoscopy system in dependence on the recognized image recording situation.

In other words, the invention thus proposes that the image recording system make a proposal to the user on the basis of computer-implemented image recording situations that are predefined on the basis of parameters, for example optically or acoustically, that in the recognized image recording situation results in an adaptation of the image processing algorithm and/or an adaptation of an image recording method, on which the recording of the image sequence is based.

It can be provided that the proposal is also automatically implemented even without the user accepting it, for example after a certain period of time has elapsed. However, the method is preferably designed such that the proposal is only implemented if it is actually accepted by a user, which will be explained in more detail.

The automatic function adaptation of the image recording system achieved by the method has the advantage that the user can use a respective meaningful functional scope of the image recording system very rapidly in changing image recording situations.

For this purpose, the image recording system can automatically propose reasonable proposals to a user depending on the context and situation for adapting the image processing algorithm and/or an image recording method used during the recording of the image sequence. The user therefore no longer has to cumbersomely find the corresponding functional adaptation by means of a user interface, such as a graphic menu, and then manually implement it himself, for which purpose it is possible that numerous adaptations are to be performed. Rather, by accepting the proposal, the user can very rapidly select an image recording and/or image display method optimum for the current image recording situation, and can do so within the full functional scope offered by the image recording system. This makes it possible to use the full functional scope in practice.

It is very particularly advantageous here if the proposed adaptation relates to a plurality of parameters of the image processing algorithm and/or the image recording method. These multiple parameters would normally have to be individually adapted manually by the user in succession. However, by way of the invention, the user can accept the adaptation proposal by means of a single confirmation input, for example, and thus set all of these parameters, for example, 10 or more parameters, simultaneously. The user therefore no longer has to perform multiple time-consuming confirmation inputs.

An artificial intelligence, which is provided by the image recording system, can ensure that the set of parameters proposed in each case is optimally adapted to the specifically recognized image recording situation. The functionality of the image recording system can thus be adjusted very rapidly to the present requirements.

The proposal is preferably accepted by means of a manual or virtual operating element.

If the image recording system is designed, for example, as an endoscopy system, this operating element can preferably be embodied on a handle of an endoscope of the endoscopy system. A user can thus perform a confirmation input to accept the proposal without having to release the endoscope from the hand, which further simplifies and accelerates the operation.

According to the invention, the object can also be achieved by further advantageous embodiments according to the dependent claims.

The adaptation proposal can thus be presented acoustically and/or visually to the user, but preferably by means of a graphic user interface on the display unit. This can be done in particular by means of an overlay that is displayed to a user on the display unit above or next to a live video image generated from the image sequence.

Furthermore, the image recording system can only make the proposed adaptation in response to a confirmation input of the user. Furthermore, it can be provided that the image recording system no longer presents an offered adaptation proposal after a predetermined period of time has elapsed. These features thus implement an error exclusion mechanism that can prevent incorrect operation, since the adaptation proposal can only be accepted by a user within a predetermined period of time by means of the confirmation input.

The confirmation input can also be made by operating an operating element, for example an operating button on a setting wheel or the like, or else a graphic user interface, i.e., in particular virtual operating buttons.

Other options which can additionally or alternatively be used are that the confirmation is performed by a voice command and/or by a gesture of the user. Such voice commands or gestures can be read out by means of a sensor of the image recording system. The image recording system can in particular have an acceleration sensor for the detection of gestures. If the image recording system is designed as an endoscopy system having an endoscope, it is thus advantageous if this acceleration sensor is arranged in the endoscope.

It can furthermore be provided that a user can reject the adaptation proposal by means of a rejection input. In response to this rejection input, the adaptation cannot then be made.

According to a further variant, it is provided that a proposed adaptation is automatically implemented by the image recording system after a predetermined period of time, if a user does not reject an associated adaptation proposal within the period of time by means of a rejection input.

It can furthermore also be provided that the user can actively reject the adaptation proposal by means of a rejection input. In this case, the imaging system will not make the proposed adjustment.

In response to the rejection input, which can be done in the same way as the confirmation input by means of operating buttons, voice commands, or gestures, a presentation of the adaptation proposal can be ended, for example by hiding a corresponding display element in a graphic user interface.

The adaptation of the image processing algorithm can comprise a replacement of the image processing algorithm. Furthermore, however, it can also only implement a re-parameterization of the image processing algorithm.

In order to be able to offer a functionality of the image recording system that is adapted to the recognized image recording situation, the image processing algorithm that is adapted by the method can adjust at least one image parameter to improve the display of the image sequence. Such an image parameter can be, for example, a color spectrum, an image sharpness, an image brightness, an image color, an image contrast, a noise component, an edge steepness, or a comparable parameter.

By adapting such image parameters, an image quality of the image sequence can be improved by the adaptation.

The image processing algorithm can in particular be a noise suppression algorithm or a filter algorithm. Combinations of such algorithms can also be used to improve the display of the image sequence.

According to one specific variant, the image processing algorithm can only be applied to a respective image section of individual images of the image sequence. It is preferred here if the image recording system proposes to the user the image section to be changed by the image processing together with the adaptation in dependence on the recognized image recording situation and/or in dependence on recognized image characteristics. Such image characteristics can be, for example, patterns, colors, structures, specific objects, or the like.

For example, the image evaluation can be designed in such a way that the image recording system recognizes the occurrence of smoke in the image sequence on the basis of the image evaluation and accordingly proposes switching on a smoke suppression algorithm. The display of the smoke in the image sequence can be suppressed using the smoke suppression algorithm, so that a user has an improved view of a scene observed using the image sensor in spite of the smoke development.

The recognition of the image recording situation can in principle, additionally or alternatively to the computer-implemented image evaluation, be performed on the basis of an activation of an external device and/or on the basis of a sensor signal. Such an activation can be, for example, switching on, for example, of an operation instrument. The sensor signal can originate from a sensor of the image recording system or from an external sensor.

For example, the above-explained occurrence of smoke can also be detected preventively by the image recording system with the aid of a switching-on procedure of an operating instrument, for example, an HF scalpel, or a sensor signal, for example, of an optical smoke sensor. The above-described adaptation proposal for switching on a smoke suppression algorithm can thus in particular take place in reaction to a performed activation of an operating instrument and/or on the basis of a signal of a smoke sensor.

If an adaptation of the image recording method is proposed, it can thus effectuate a change of an image recording parameter. Such image recording parameters are, for example, a shutter speed of the image sensor or a sensitivity of the image sensor. Furthermore, the adaptation of the image recording method can also effectuate an adaptation of an illumination which is used when recording the image sequence.

According to one special design, a change of an illumination method and/or an imaging method, which is respectively used to record the image sequence, can be carried out by the adaptation of the image recording method.

According to one preferred design, the adaptation of the image recording method effectuates a change from white light imaging to narrowband imaging (NBI), wherein NBI takes place using spectral illumination. The adaptation can furthermore also cause a reverse change from NBI to white light imaging.

According to a further aspect of the present invention, the computer-implemented image evaluation can be based in particular on artificial intelligence (AI) for recognizing specific image recording situations. These image recording situations can, in particular, be parameterized, i.e., defined by predetermined, in particular trained parameter sets.

According to one preferred design, the AI is implemented by means of a neural network. Alternatively or additionally, the AI can also be implemented by means of an algorithm which has been trained with the aid of example image sequences, in particular under human instruction.

According to the invention, the AI can be used to recognize a specific image recording situation, to then be able to suggest a corresponding adaptation proposal designed for the recognized image recording situation.

The computer-implemented evaluation of the recorded image sequence can furthermore be based on a comparison of at least one probability parameter obtained from the image sequence to an associated threshold value in each case. If three probability parameters are used, for example, three different respective associated threshold values can thus be provided. Such probability parameters can be obtained, for example, by a parameterization of the image sequence, for example, based on color, movement, structure, or pattern recognition or the like. Such a parameterization can preferably be provided by an image processing unit of the image recording system.

It can furthermore be provided that the image recording system only suggests an adaptation proposal if the at least one threshold value is exceeded. Furthermore, otherwise generating or offering the adaptation proposal can be omitted.

With such a design, it is preferred if the image recording system only suggests an adaptation proposal if the threshold values are exceeded. An overload of the user by excessively frequent proposals is thus avoided. This is because an adaptation of the image processing algorithm and/or the image recording method used when recording the image sequence can be omitted if the threshold values are not exceeded.

In this case, it is preferred if the at least one probability parameter is obtained with the aid of an algorithm which also implements an artificial intelligence that is trainable in particular.

As already outlined above, in response to an activation, for example, switching on, of an external device such as an electrosurgical operation instrument, a display of the image sequence adapted to the external device and/or an image recording method adapted to the external device can furthermore be proposed to a user by the image recording system. Such an adaptation can be, for example, smoke suppression based on image processing or an adaptation of image recording parameters.

Adaptations as described above can be carried out in particular in such a way that a user of the image recording system accepts or rejects the offered adaptation proposal via a respective operating element to adapt the display of the image sequence and/or the type of the image recording accordingly. For this purpose, the image recording system can be in continuous contact with the external device, for example via a cable or a wireless connection.

The computer-implemented image evaluation of the recorded image sequence can furthermore include a context-based data analysis of the image sequence. This has the advantage that certain types of image recording situations can be better recognized on the basis of their respective context.

The image recording system which carries out the image recording method according to the invention can in particular have a permanently stored catalog of adaptation proposals which can be each suggested to a user in response to a recognized image recording situation. This catalog can in particular be stored in an internal storage medium of the image recording system.

Adaptation proposals critical for the use of the image recording system from a first class can preferably only be offered upon reaching a preset or settable statistical minimum certainty in the recognition of the image recording situation by the image recording system. Noncritical adaptation proposals from a second class can already be offered with a statistical certainty below the minimum certainty.

Such a critical adaptation can consist, for example, of overlaying additional image channels, i.e., such as items of image information which have been recorded using other examination methods such as magnetic resonance tomography (MRT), computer tomography (CT), fluorescence imaging, chromoendoscopy, or other methods.

Such overlays are critical because there is a risk that the important items of information in a live video image continuously observed by the user of the image recording system will be concealed by the overlay, i.e., the arrangement of operation instruments in relation to vulnerable tissue structures or the like. By providing a statistical minimum certainty, which can be determined in particular by one or more probability parameters obtained from the image processing, as described above, it is possible to prevent an adaptation proposal not suitable for the situation from being generated and possibly even accepted and thus an avoidable malfunction from occurring, which prevents the user from correctly operating and using the image recording system.

Furthermore, the features of the independent device claim are provided according to the invention for achieving the mentioned object. In particular, it is thus proposed according to the invention in an image recording system as introduced at the outset that the image recording system comprises an image processing unit, which is configured to recognize at least one image recording system, but preferably a plurality of predefined image recording systems, in the image sequence by means of automatic image evaluation, and that the controller is configured to generate a proposal for adapting the image processing algorithm and/or for adapting an image recording method used when recording the image sequence in dependence on the recognized image recording situation.

Furthermore, it can be provided that the controller is configured to present this adaptation proposal to a user, preferably with the aid of a graphic user interface on the display unit.

For this purpose, the controller can preferably be arranged or embodied in a camera control unit of the image recording system. The display unit can be implemented, for example, by an external monitor.

In all of these cases, it is very particularly advantageous if the controller is configured to execute one of the above-described methods. This is because the advantages of the invention can thus be fully utilized by the image recording system.

The image processing unit can be implemented, for example, locally in a camera control unit of the image recording system or, for example, in an external local processing unit. However, the image processing unit can also be outsourced. The image processing unit can thus also, for example, be implemented by means of a local server network or by means of a "cloud solution", i.e., by means of an IT infrastructure available via the Internet.

The invention will now be described in greater detail on the basis of exemplary embodiments, but is not restricted to these exemplary embodiments. Further embodiments of the invention can be obtained from the following description of a preferred exemplary embodiment in conjunction with the general description, the claims, and the drawings.

In the following description of various preferred embodiments of the invention, functionally corresponding elements have corresponding reference signs even if they have a different design or shape.

DETAILED DESCRIPTION

Figure 1:
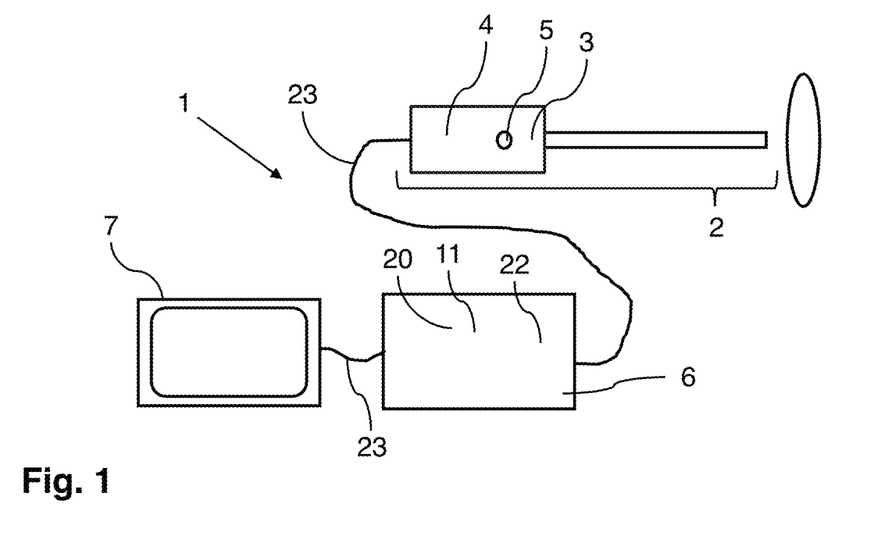
FIG. 1 shows an image recording system according to the invention in the form of an endoscopy system.

FIG. 1 shows an image recording system 1 according to the invention in the form of a video endoscopy system 1, which comprises an endoscope 2 having an image sensor 3 for recording an image sequence 18 in the form of a video image datastream and a controller 20. The image sensor 3 is arranged in a camera head 4 of the endoscope 2.

The controller 20 is configured to control an image processing algorithm that is applied to the image sequence 18 in order to improve a display of the image sequence 18 on a display unit 7, which is connected via a cable 23 to a camera control unit 6 of the endoscopy system 1. This image processing algorithm comprises a noise filter and an algorithm for increasing the image contrast, so that the video image datastream can be reproduced by the display unit 7 in high image quality as a live video image 21.

An image processing unit 11 is formed in the camera control unit 6 of the endoscopy system 1, which is configured to recognize a variety of predefined image recording situations in the image sequence 18 by means of an automatic image evaluation. For this purpose, the image processing unit 11 monitors the continuously generated video image data stream and evaluates it in a computer-implemented manner. If the image processing unit 11 recognizes one of the predefined image recording situations, the controller 20 thus generates in response to this a proposal for adapting the image processing algorithm.

The recognition of the image recording situation is based on an artificial intelligence (AI), which is based on an algorithm that has been trained in advance by an operator on the basis of exemplary video image recordings of surgical interventions. Through the training, the AI has learned which concrete parameter sets can be used to characterize a specific recording situation.

Correspondingly, a catalog of predefined image recording situations in the form of the trained parameter sets was stored in a storage medium 22 of the endoscopy system 1. The image processing unit 11 uses this catalog during the computer-implemented evaluation of the image sequence 18 and can thus recognize a large number of image recording situations at high speed with high accuracy.

A catalog of adaptation proposals is furthermore stored in the storage medium 22, wherein a specific adaptation proposal is associated with each of the stored image recording situations. Depending on the recognized image recording situation, the endoscopy system 1 can thus suggest an adaptation proposal appropriate for the respective image recording situation.

The adaptation proposals are divided into two classes, namely into critical and noncritical adaptation proposals. Critical adaptation proposals are only proposed by the endoscopy system 1 if the associated image recording system has been recognized with a statistical minimum certainty. This minimum certainty is ascertained on the basis of probability parameters that are compared to stored threshold values. A critical adjustment proposal is only proposed if all threshold values are exceeded, which are checked for the specific image recording situation.

These adaptation proposals are each visualized for user of the endoscopy system 1 on the display unit 7 by means of graphic display elements 16, as will be explained in more detail on the basis of FIGS. 3 to 6. The user can then accept or reject the offer proposal or do nothing at all. In the latter case, the proposal is only implemented if the user accepts the proposal within a predetermined period of time.

Figure 5:
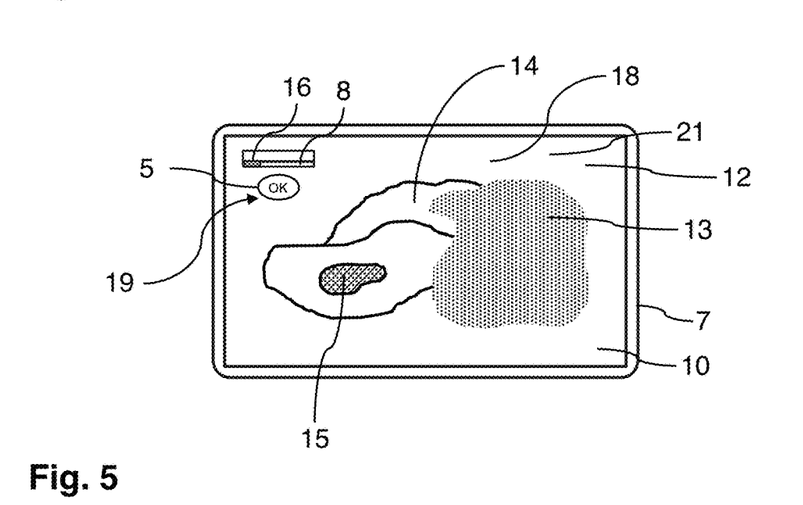
FIG. 5 shows the display unit from FIG. 3 in a third display situation.

A typical image recording situation that the image processing unit 11 can recognize is illustrated in FIG. 5. FIG. 5 shows a first display situation which is displayed by the display unit 7. The live video image 21 can be seen, which is displayed in a display area 12 specially provided for this purpose. Furthermore, a time lapse display 8 and a virtual operating element 5 in the form of a virtual OK button can be seen.

The user can recognize both healthy tissue 14 and also malignant tissue 15 in the live video image 21 (cf. FIG. 5). This malignant tissue 15 is just about to be resected using an HF scalpel. Due to the development of heat when cutting using the HF scalpel, a cloud of smoke 13 has arisen, which partially blocks the view of the tissue structures.

Based on the computer-implemented evaluation of the recorded image sequence 18, the endoscopy system 1 has recognized the specific image recording situation "smoke in the image". Accordingly, a specific proposal for adapting the image processing algorithm has been proposed, namely the expansion of the image processing algorithm by an additional smoke suppression algorithm.

This proposal is presented to the user optically by means of a graphic user interface on the display unit 7, as shown in FIG. 5. For this purpose, the display element 16, which can be seen in the upper left corner in FIG. 5, is provided, which explains to the user which specific function can now be added thereto.

By means of the time-lapse display 8, the user is simultaneously shown how much time he has left to accept the offered proposal. If the user accepts the proposal by touching the virtual OK button (=confirmation input 19) within the period of time specified by the time-lapse display 8, the endoscopy system 1 thus switches on the smoke suppression function and the display situation illustrated in FIG. 6 results. The additional function just added thereto is visualized for the user by means of a further display element 16, which can be seen in the top middle in FIG. 6.

Figure 6:
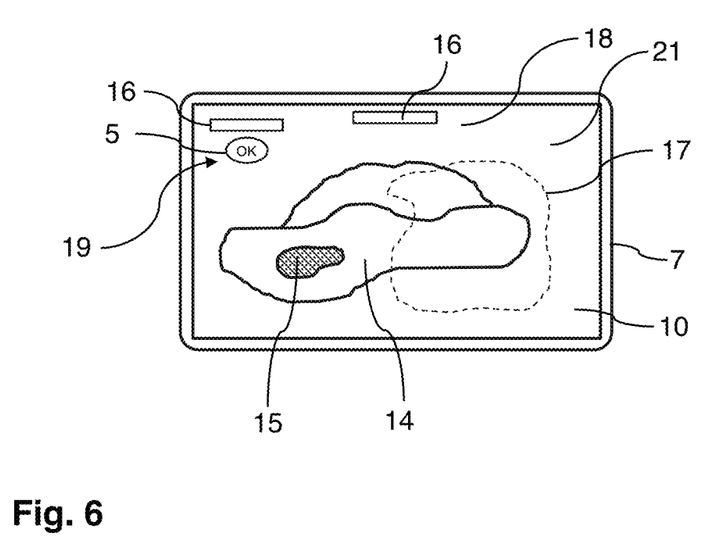
FIG. 6 shows the display unit from FIG. 3 in a fourth display situation.

As can be seen in FIG. 6, the endoscopy system 1 has detected the smoke cloud by means of image processing and has deliberately applied the smoke suppression algorithm to the image section 17 which was occupied by the cloud of smoke 13. For this purpose, the endoscopy system 1 has previously proposed to the user, with the aid of the dashed line shown in FIG. 6 on the basis of the object "smoke cloud" recognized in the live video image 21—together with the proposed adaptation—the image section 17 to be changed by the image processing. The user has also accepted this proposal by way of a corresponding user input 19 (i.e., by once again touching the operating element 5), so that, for example, the smoke suppression algorithm has not inadvertently been applied to image regions in which no smoke 13 was recognized.

As can be seen from the live video image 21 in FIG. 6, the use of the smoke suppression function has decisively improved the image quality, so that structures behind the cloud of smoke 13 can now also be recognized by the user. In other words, the image processing algorithm was thus adapted such that an image parameter of the live video image 21 was adapted for improved display.

In contrast to previous systems, the user did not have to search extensively in submenus for this purpose, but rather the additional function appropriate for the specific recognized image recording situation "smoke in the image" of a smoke suppression was proposed to him for acceptance in a manner adapted to the situation by the endoscopy system 1, namely by means of a visual indication with the aid of the display element 16.

Figure 3:
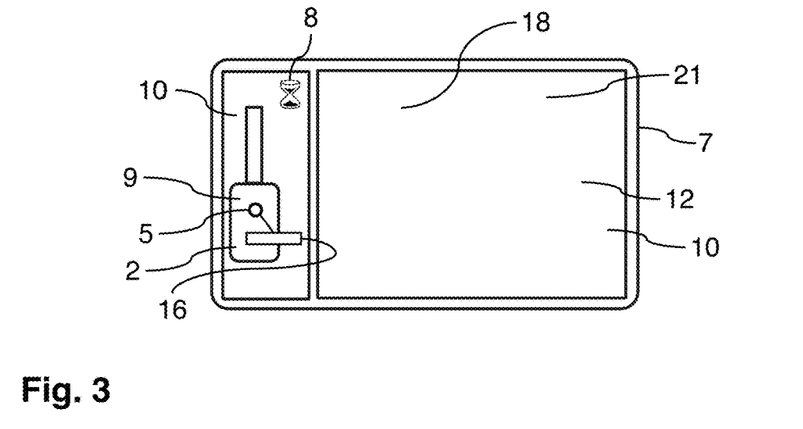
FIG. 3 shows a display unit in a first display situation.

FIG. 3 shows a further possibility of how an adaptation proposal can be visually presented to a user. For this purpose, a separate window 10 is provided, in which a pictogram 9 of the endoscope 2 is depicted. This shows the user the spatial position of the control element 5, using which he can accept the presently offered adaptation proposal. The adaptation proposal is described here with the aid of a display element 16.

Figure 4:
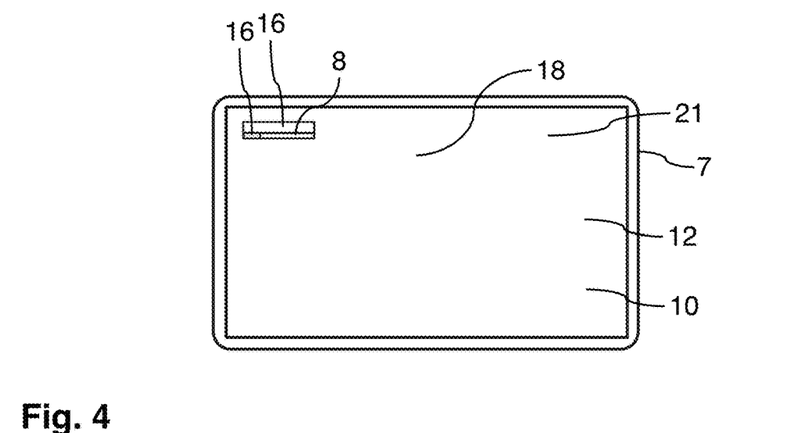
FIG. 4 shows the display unit from FIG. 3 in a second display situation.

FIG. 4 illustrates a further option for suggesting an adaptation proposal. A time window is visualized here for the user with the aid of a display element 16 and a time-lapse display 8, within which the adaptation proposal presented by the display element 16 is automatically implemented by the endoscopy system 1 if the user does not actively reject the proposal by means of a rejection input. Such a design can make sense, for example, in specific operating situations, since an operator does not have to actuate a confirmation input here to accept the adaptation proposal.

The user can preferably also accept the adaptation proposal by means of the further operating element 5 apparent in FIG. 1 in the form of a manual rocker button or by the voice command "accept proposal", wherein the endoscopy system 1 then switches on the proposed smoke suppression function in reaction to this respective confirmation input 19 and thus effectuates an adaptation of the image processing algorithm.

The endoscopy system 1 is furthermore capable of adapting not only the image processing algorithm, but rather a method which is used to record the image sequence 18.

For example, the endoscopy system 1 can first record conventional color images by means of a white light illumination. If an optical sensor of the endoscope 2 detects the emission of fluorescent light by the observed tissue, the endoscopy system 1 thus proposes to the user an adaptation of the image recording method such that the illumination is switched over from white light to a spectral illumination using excitation light. In addition, in this case it is proposed to the user by means of a further display element 16 that the image recording method used be switched over from white light imaging to narrowband imaging (NBI).

If the user accepts both of these adaptation proposals, white light images are no longer displayed on the display unit 7, but rather fluorescent light images which are now recorded by means of NBI by the endoscopy system 1. In addition, in response to the confirmation input 19, the endoscopy system 1 has adapted a sensitivity and a shutter speed of the image sensor 3, that is to say 2 image acquisition parameters, to the new NBI method. A change of the illumination and imaging methods used for recording the image sequence 18 has thus taken place due to the performed adaptation.

For this change, the endoscopy system 1 has therefore not just evaluated the recorded video image data stream in a computer-implemented manner, but instead has recognized the new image recording situation "fluorescent light present in the image" on the basis of a sensor signal of the optical sensor. This alternative detection of a new image recording situation can be used independently of the computer-implemented evaluation of the image sequence, but preferably in addition to it.

Figure 2:
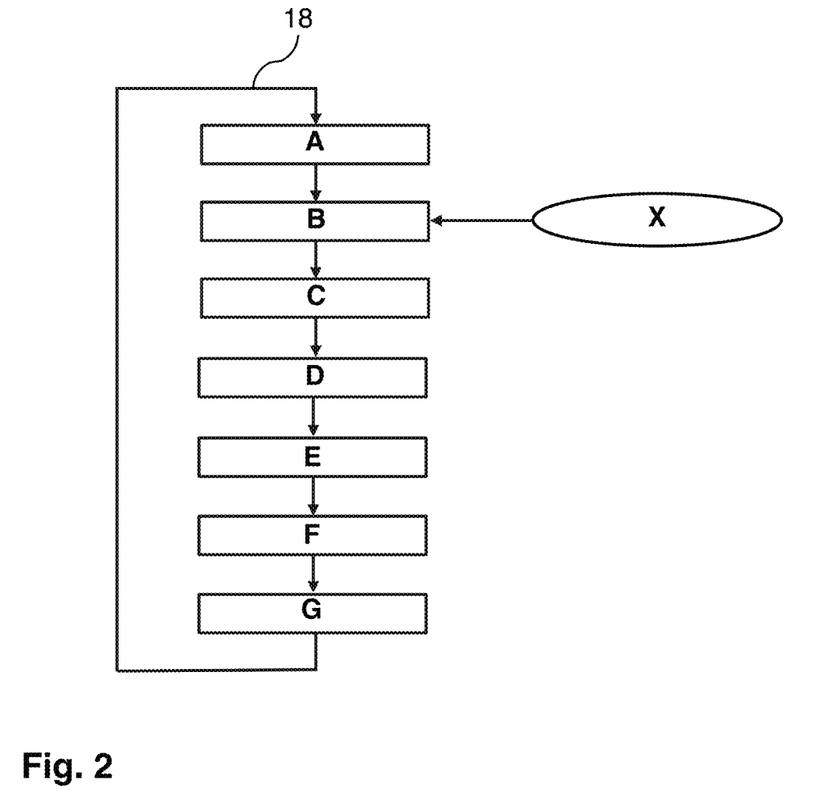
FIG. 2 shows a signal flow chart to explain an endoscopy method according to the invention.

Finally, FIG. 2 explains, on the basis of the signal flow chart shown, a practical implementation of an image recording method according to the invention by way of the following method steps:

a. recording the image sequence 18 using the image recording system 1 in the form of a video image data stream;
b. computer-implemented evaluation of the image sequence 18 with the aid of the image processing unit 11;
c. calculation of image parameters and probability parameters based on the evaluation;
d. comparison of the probability parameters to threshold values;
e. generating an adaptation proposal;
f. offering the adaptation proposal;
g. acknowledging the proposed adjustment proposal by accepting, rejecting, or doing nothing;

doing nothing in the last step G is considered a rejection. If the adaptation proposal is accepted, the proposal is immediately implemented by the endoscopy system as proposed. Step D is an optional step and step E does not take place unless a predefined image recording situation has been detected or only with insufficient certainty, which is determined on the basis of the threshold value comparison. Step F is preferably carried out visually, for example with the aid of a display element 16, or for example acoustically. Finally, the further optional step X comprises the use of an artificial intelligence in the computer-implemented evaluation of the recorded image sequence, as was described in detail above.

In summary, to simplify the use of a functional scope of a medical image recording system 1, for example an endoscopy system 1, a method is proposed in which an image processing unit 11 of the image recording system 1 recognizes predefined image recording situations on the basis of an image sequence 18 recorded using an image sensor 3 of the image recording system 1 and in response thereto proposes an adaptation to a user that results in an improved display and/or recording of the image sequence 18 in the respective recognized image recording situation. The adaptation can relate here to an algorithm, using which the image sequence 18 is processed after the recording, and/or an image recording method currently used to generate the image sequence 18.

What is claimed:

1. An image recording method, in which an image sequence, including the form of a video image datastream, is recorded using an image sensor of a medical image recording system; wherein the image sequence is subjected to an image processing algorithm, even before it is displayed on a display unit, to improve the display of the image sequence; wherein the recorded image sequence is evaluated in a computer-implemented manner based on artificial intelligence which recognizes specific image recording situations; wherein a catalog of predefined image recording situations in the form of trained parameter sets is stored in a computer-readable storage medium such that the different specific image recording situations are predefined on the basis of said parameters; and, wherein, depending on an image-recording situation recognized by the computer-implemented image evaluation, a corresponding adaptation of the image processing algorithm and/or an adaptation proposal comprising of an adaptation of the image recording method used when recording the image sequence is automatically proposed to a user.

2. The image recording method as claimed in claim 1, wherein the adaptation proposal can be presented acoustically and/or optically to the user for acceptance, including by a graphic user interface on the display unit.

3. The image recording method as claimed in claim 1, wherein the image recording system only carries out the adaptation proposal in response to a confirmation input by the user, and wherein the image recording system no longer presents an offered adaptation proposal after passage of a predetermined period of time.

4. The image recording method as claimed in claim 3, wherein the confirmation input is performed by operating an operating element, including an operating button or the graphic user interface, and/or by a voice command and/or by a gesture of the user, read out by the image sensor of the image recording system, and including an acceleration sensor of an endoscope.

5. The image recording method as claimed in claim 1, wherein the user can reject the adaptation proposal by a rejection input, whereupon the adaptation proposal is not carried out, and/or wherein the adaptation proposal is automatically implemented by the image recording system after a predetermined period of time if the user does not reject an associated adaptation proposal within the period of time by the rejection input.

6. The image recording method as claimed in claim 1, wherein the adaptation proposal of the image processing algorithm comprises a replacement of the image processing algorithm, or a reparameterization of the image processing algorithm.

7. The image recording method as claimed in claim 1, wherein the image processing algorithm adapts at least one image parameter, including a color spectrum, an image sharpness, an image brightness, an image color, an image contrast, a noise component, an edge steepness, or the like for improved display of the image sequence, including that an image quality of the image sequence is improved by the adaptation, and/or wherein the image processing algorithm is a noise suppression and/or filter algorithm.

8. The image recording method as claimed in claim 1, wherein the image processing algorithm is solely applied to a respective image section of individual images of the image sequence, and wherein the image recording system proposes, together with the adaptation, the image section to be changed by the image processing to the user in dependence on the recognized image recording situation and/or recognized image characteristics, including patterns, colors, structures, objects, or the like.

9. The image recording method as claimed in claim 1, wherein additionally or alternatively to the computer-implemented image evaluation, the recognition of the image recording situation is carried out on the basis of a performed activation, including switching on, of an external device, including an operating instrument, and/or on the basis of a sensor signal.

10. The image recording method as claimed in claim 1, wherein the adaptation proposal of the image recording method effectuates a change of an image recording parameter, including a shutter speed of the image sensor, a sensitivity of the image sensor, or an adaptation of an illumination used for recording the image sequence, and/or wherein a change of an illumination and/or imaging method used for recording the image sequence is carried out by the adaptation of the image recording method.

11. The image recording method as claimed in claim 1, wherein the adaptation proposal of the image recording method effectuates a change from white light imaging to narrowband imaging (NBI) using spectral illumination or a reverse change.

12. The image recording method as claimed in claim 1, wherein the computer-implemented image evaluation is based on an artificial intelligence for recognizing specific, parameterized image recording situations, and wherein the artificial intelligence is implemented by means of a neural network and/or by an algorithm which has been trained with the aid of example image sequences, including under human instruction.

13. The image recording method as claimed in claim 1, wherein the computer-implemented image evaluation of the recorded image sequence is based on a comparison of at least one probability parameter obtained from the image sequence to a respective associated threshold value, wherein the image recording system only suggests an adaptation proposal if the threshold value is exceeded, preferably wherein the at least one probability parameter is obtained with the aid of an algorithm which implements an artificial intelligence that is trainable in particular.

14. The image recording method as claimed in claim 1, wherein the computer-implemented image evaluation of the recorded image sequence comprises a context-based data analysis of the image sequence.

15. The image recording method as claimed in claim 1, wherein the image recording system has a permanently stored catalog of adaptation proposals in an internal storage medium, which can each be suggested to the user in response to a recognized image recording situation, and wherein adaptation proposals critical for the use of the image recording system from a first class are only offered upon reaching a preset or settable statistical minimum certainty in the recognition of the image recording situation by the image recording system, while noncritical adaptation proposals from a second class can already be offered at a statistical certainty below the minimum certainty.

16. A medical image recording system, comprising:
an image sensor for recording an image sequence;
a controller for controlling an image processing algorithm, which is applied to the image sequence in order to improve a display of the image sequence on a display unit;
wherein the image recording system further comprises an image processing unit;
wherein said image processing unit is configured to recognize at least one specific image recording situation via an artificial intelligence trained via parameter sets stored in a computer-readable storage medium such that the different specific image recording situations are predefined on the basis of said parameter sets; and,
wherein the controller is configured to generate a corresponding proposal for adapting the image processing algorithm and/or an image recording method used when recording the image sequence in dependence on the recognized at least one image recording situation provided by the image processing unit.

17. The image recording system as claimed in claim 16, wherein the controller is configured to carry out a method as claimed in claim 1.

18. The image recording system as claimed in claim 16, wherein the image processing unit is implemented in a camera control unit of the image recording system or in an external local processing unit or by a local server network or via an IT infrastructure which is available via the Internet (cloud).

* * * * *